US00PP16744P2

(12) United States Plant Patent
Olesen et al.

(10) Patent No.: US PP16,744 P2
(45) Date of Patent: Jul. 4, 2006

(54) COMPACT FLORIBUNDA ROSE VARIETY 'POULYMP'

(50) Latin Name: ***Rosa* hybrid**
Varietal Denomination: POULymp

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 09/607,327

(22) Filed: Jun. 30, 2000

(51) Int. Cl.
*A01H 5/00* (2006.01)

(52) U.S. Cl. ..... Plt./145
(58) Field of Classification Search ..... Plt./145
See application file for complete search history.

(56) References Cited

PUBLICATIONS

UPOV–ROM GTITM Computer Database, 2001/02, GTI Jouve Retrieval Software, citation for 'POULymp'.*
Printed advertisement page from internet site: www.poulsenroser.dk, dated: May 31, 2005. (1 page).

Community Plant Variety Office "Proposal for a Variety Denomination" Jan. 26, 1999 EU 2 pages.

Community Plant Variety Office "UPOV Extract" EU 4 pages.

Community Plant Variety Office "Chapter II: Variety Denominations" Apr. 15, 1999 2 pages.

Community Plant Variety Office "Certificate On The Grant . . . " Jun. 19, 2000.

Canadian Food Inspection Agency "Applications Acceppted for Filing" Jan. 1999 Canada 1 page.

* cited by examiner

*Primary Examiner*—Bruce R. Campell
*Assistant Examiner*—S. B. McCormick-Ewoldt

(57) ABSTRACT

A new Floribunda rose plant which has abundant, bronze flowers and attractive foliage. The variety successfully propagates from softwood cuttings and is suitable for year round production in commercial glasshouses. This new and distinct variety has shown to be uniform and stable in the resulting generations from asexual propagation.

2 Drawing Sheets

Botanical classification: '*Rosa* hybrid'.
Variety denomination: 'POULymp'.

SUMMARY OF THE INVENTION

The present invention constitutes a new and distinct variety of Floribunda rose plant which originated from a controlled crossing between an unnamed seedling and an unnamed seedling. The two parents were crossed and the resulting seeds were planted in a controlled environment. The new variety is named 'POULymp'.

The new rose may be distinguished from its seed parent,, by the following combination of characteristics:

1. The unnamed seed parent's flowers are yellow, where those of 'POULymp' are more golden bronze in color.
2. The growth of the unnamed seed parent is more vigorous than that of 'POULymp'.

The new variety may be distinguished from its pollen parent, created by the same inventors, by the following combination of characteristics:

1. The unnamed pollen parent's flowers are yellow, where those of 'POULymp' are a golden bronze color.
2. The growth of the pollen parent is more vigorous than that of 'POULymp'.

The objective of the hybridization of this rose variety for commercial greenhouse culture was to create a new and distinct variety with unique qualities, such as:

1. Uniform and abundant flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type and distinguish 'POULymp' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark. 'POULymp' was selected by the inventors as a single plant from the progeny of the hybridization in Fredensborg, Denmark, in the spring of 1996.

Asexual reproduction of 'POULymp' by cuttings and traditional budding was first done by L. Pernille and Mogens N. Olesen in their nursery in Fredensborg, Denmark in . This initial and other subsequent propagations conducted in controlled environments have demonstrated that the characteristics of 'POULymp' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, stems, and a plant of 'POULymp'. Specifically illustrated in SHEET 1:

1. Stem or entire plant showing branching and the attachment of leaves, buds, and peduncles;

2. Flower bud, partially opened bud, and open bloom;

3. Flower petals, detached;

4. Sepals, receptacle, and pedicel;

5. Flowering stem as well as a bare stem exhibiting thorns;

6. Leaves.

DETAILED DESCRIPTION OF THE VARIETY

The following is a description of 'POULymp', as observed in its growth in glasshouses in Half Moon Bay, Calif. Observed plants are 3 months in age. Color references are made using The Royal Horticultural Society (London, England) Colour Chart, 1995, except where common terms of color are used.

For a comparison, several physical characteristics of the rose variety 'POULsail', a Compact Floribunda rose variety from the same inventors described and illustrated in U.S. Plant patent application Ser. No. 09/140,630 dated Aug. 26, 1998, are compared to 'POULymp' in Chart 1.

CHART 1

| | 'POULymp' | 'POULsail' |
|---|---|---|
| Bud Color, ¼ Open | Orange-Red Group 35A with overlay of Greyed-Red Group 179 B-C. | Red Group 39A to 43C. |
| Open flower bloom color, upper petal surface. | Yellow-Orange Group 21C. | Red Group 41C. |
| Open flower bloom petal color, reverse side. | Orange-Red Group 35C. | Red Group 41C. |

Parents: Unnamed Seedling×Unnamed Seedling.

Classification:

*Botanical.*—*Rosa* hybrid.

*Commercial.*—Floribunda.

FLOWER AND FLOWER BUD

Blooming habit: Continuous.

Flower bud:

*Size.*—Upon opening, 32 mm–36 mm in length from base of receptacle to end of bud.

*Bud form.*—The bud form is initially high centered, and pointed. Once sepals drop/open half way, then bud is cylindrical.

*Bud color.*—As sepals unfold, blend of Greyed-Red Group 179B–C and Orange-Red Group 35A. Blend of Greyed-Red Group 179C and Orange-Red Group 35A at ¼ opening.

*Sepals.*—Green Group 137A. Weak foliaceous appendages on three of the five sepals. Surfaces of sepals slightly pubescent. Few Stipitate glands are present. Distal ends of sepals have foliaceous appendages. Sepals are 25 to 35 mm in length and 10 to 13 mm wide.

*Receptacle.*—Surface: Smooth. Shape: Broadly funnel shaped. Size: 7 mm (h)×8–9 mm (w). Color: Green Group 138 A.

*Peduncle.*—Surface: Smooth. Length: 50–70 mm average length. Color: Green Group138 A. Strength: Upright.

*Borne.*—Generally with single buds per flowering stem.

Flower bloom:

*Fragrance.*—Light Spice scent.

*Duration.*—As a pot plant, flowers last from 14 to 21 days. As a cut flower to days. The blooms have a duration on the plant of approximately to days.

*Size.*—Large for a 15 cm pot rose. Average flower diameter is 60–70 mm when open.

*Form.*—Cylindrical during opening.

*Shape of flower when viewed from the side.*—Upon opening, upper part: Convex. Upon opening, lower part: Convex. Open flower, upper part: Convex. Open flower, lower part: Flat.

*Petalge.*—Double. Average range: 25–30 petals under normal conditions with 2–3 petaloids.

Color:

*Upon opening, petals.*—Outermost petals: Upper Surface: Blend of Yellow-Orange Group 20B and Orange Group 24C. Reverse Side: Orange-Red Group 32 B–C. Innermost petals: Upper Surface: Yellow Orange Group 19 A–B. Reverse Side: Orange-Red Group 32B–C.

*Upon opening, basal petal spots.*—Outermost petals: Outer Side: Yellow-Green 1C. Inner Side: Yellow-Green 1C to Yellow Group 2A. Innermost petals: Outer Side: Yellow-Green 1C. Inner Side: Yellow-Green 1C to Yellow Group 2A.

*After opening, petals.*—Outermost petals: Upper Surface: Yellow-Orange Group 21C. Reverse Side: Orange-Red Group 35C with intonations of Yellow-Orange 21C. Petals edges are Yellow Orange 21 C. Innermost petals: Upper Surface: Blend of Yellow Orange Group 20B and Orange Group 24D. Reverse Side: Orange-Red Group 34D. After opening, basal petal spots: Outermost petals: Outer Side: Yellow-Green Group 1C. Inner Side: Yellow-Green Group 1C and Yellow-Green Group 2A. Innermost petals: Outer Side: Yellow-Green Group1C. Inner Side: Yellow-Green Group 1C and Yellow-Green Group 2A.

General tonality: On open flower blend of Yellow-Orange Group 20B, Orange Group 24C, and Yellow-Orange Group 21C. No change in the general tonality at the end of 4–5 days. Afterwards, general tonality is Orange Group 24B and Yellow-Orange 16B.

*Petals.*—Petal Reflex: Strongly reflexed. Petal Margin: Slightly undulate and entire. Shape: Round. Petaloids: There are 2–3 petaloids present. Thickness: Average. Arrangement: Informal.

Reproductive organs:

*Pollen.*—Color: Greyed-Yellow Group 170C. Abundance: Average abundance.

*Anthers.*—Size: 2 to 3 mm. Color: Greyed-Yellow Group 162B–Yellow 13B. Quantity: 30 to 35.

*Filaments.*—Color: Yellow-Green Group 1C. Length: 5 mm.

*Stigmas.*—Position: Level with the height of the anthers. Quantity: 25 to 30. Color: Yellow-Green Group 145C.

*Styles.*—Color: Yellow-Green Group 145C with intonations of Greyed-Red Group 181A. Length: 5 mm.

PLANT

Plant growth: Vigorous, compact, upright. When grown as a 15 cm pot plant, the average height of the plant itself is 24 to 26 cm and the average width is 26 to 28 cm.

Stems:

*Color.*—Young wood: Green Group 137A–B. Older wood: Green Group 137A–B.

*Thorns.*—Incidence: Few thorns. Size: Average length: 5 mm–6 mm. Color: Yellow-Green Group 149D. With anthocyanin intonations of Greyed-Red Group 179C. Shape: Linear.

*Surface.*—Young wood: Smooth. Older wood: Smooth.

*Length.*—Under typical greenhouse conditions, stem length is 30 to 35 cm. Internode length varies from 10 to 12 cm.

Plant foliage: Normal number of leaflets on leaves in middle of the stem: 5 leaflets, with a range of 3–7 leaflets.

*Leaf size.*—110–120 mm (l)×85–100 mm (w).

*Abundance.*—Above average.

*Color.*—Upper Leaf Surface: Green Group 137A–139A. Lower Leaf Surface: Yellow-Green Group 147B–C.

*Juvenile foliage.*—Upper Leaf Surface: Green Group 143A–B. Lower Leaf Surface: Yellow-Green Group 146B. Anthocyanin intonation: Location: Underside leaflets, leaflet margins, rachis & petiole. Color: Greyed-Red Group 179B.

Plant leaves and leaflets:

*Stipules.*—Size: 8 mm–10 mm. Color: Green Group 137A. Stipitate glands: Stipitate glands present on margins.

*Petiole.*—Length: 24 mm–26 mm. Color: Green Group 137A. Underneath: Smooth. Margins: Stipitate glands present on margins in limited numbers.

*Rachis.*—Color: Green Group 137A. Underneath: Generally smooth, occasional prickles and stipitate glands. Margins: Regular stipitate glands present.

*Leaflet.*—Edge: Serrated. Shape: Broadly ovate. Other: Glossy and somewhat thick.

Disease resistance: Above Average resistance to mildew, black spot, and *Botrytis* under normal growing conditions in Jackson County, Oreg., Burlington, Canada, and Fredensborg, Denmark.

Cold hardiness: 'POULymp' has been found to be resistant to damage from cold, heat and drought damage in USDA Zone 7.

What is claimed is:

1. A new and distinct variety of Compact Floribunda rose, substantially as herein illustrated and described as a distinct and novel rose variety due to its abundant, bronze flowers, vigorous and compact growth, year round flowering under glasshouse conditions, suitability for production from softwood cuttings in pots, and durable flowers and foliage which make the variety suitable for distribution in the floral industry.

* * * * *

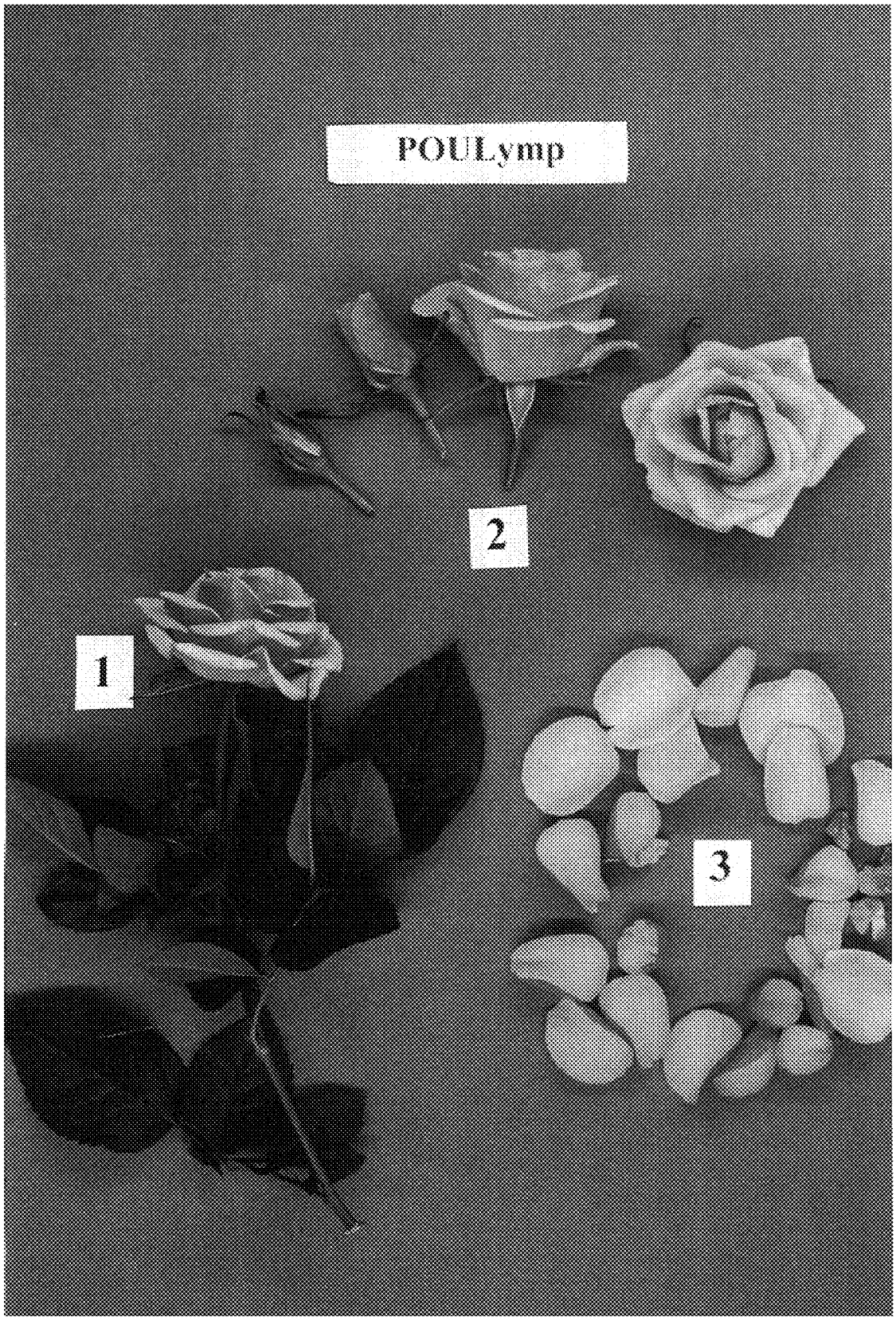
POULymp
2
1
3

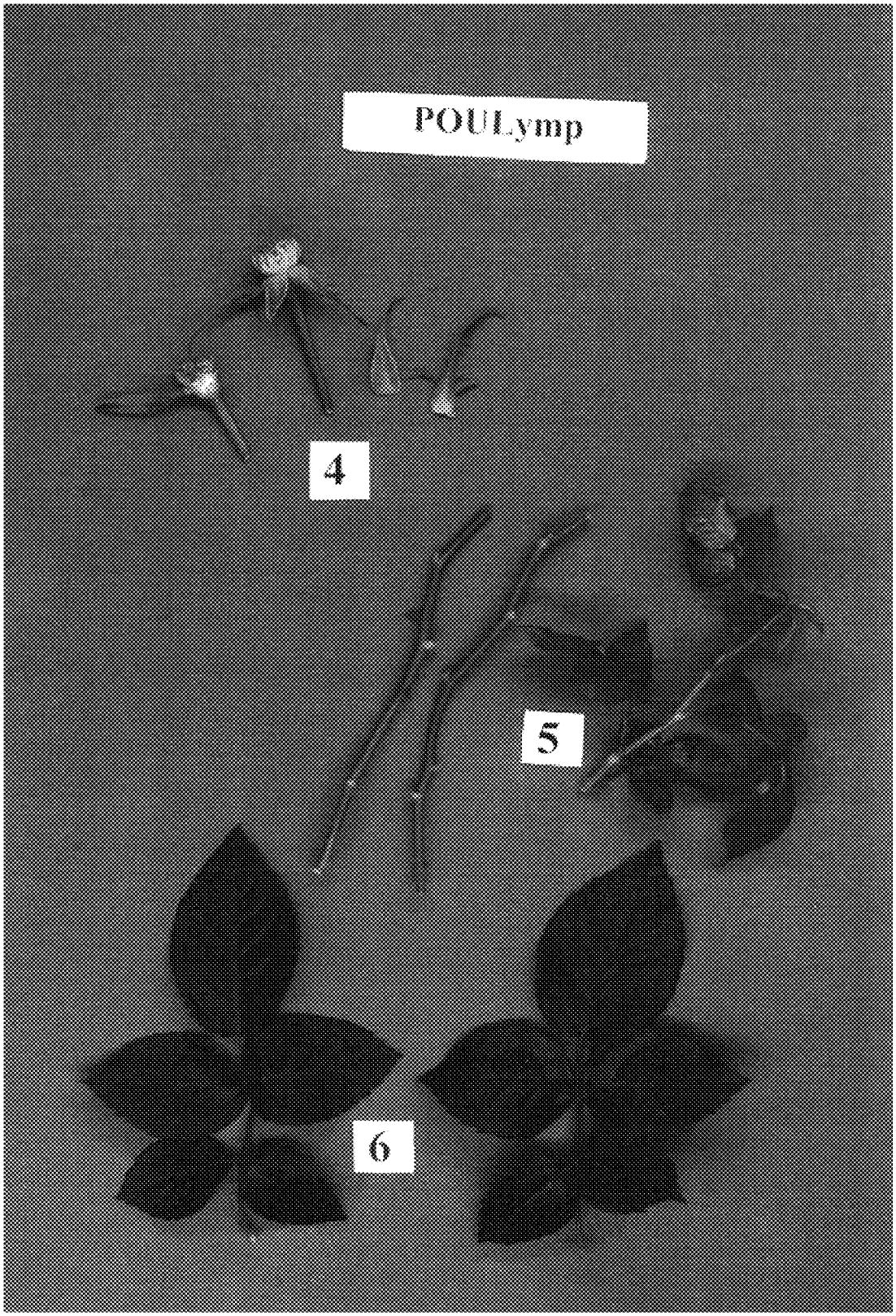
POULymp
4
5
6